United States Patent [19]

Morris

[11] Patent Number: 5,713,867
[45] Date of Patent: Feb. 3, 1998

[54] INTRODUCER SYSTEM HAVING KINK RESISTANT SPLITTABLE SHEATH

[75] Inventor: Mary M. Morris, Mounds View, Minn.

[73] Assignee: Medtronic, Inc., Minneapolis, Minn.

[21] Appl. No.: 639,660

[22] Filed: Apr. 29, 1996

[51] Int. Cl.⁶ .................................................. A61M 5/178
[52] U.S. Cl. .................................................. 604/164; 604/282
[58] Field of Search ................................... 604/282, 102, 604/134, 160, 158, 161, 164, 264, 280

[56] References Cited

U.S. PATENT DOCUMENTS

| | | | |
|---|---|---|---|
| 4,306,562 | 12/1981 | Osborne | 128/348 |
| 4,874,374 | 10/1989 | Kousai et al. | 604/164 |
| 5,176,660 | 1/1993 | Truckai | 604/282 |
| 5,380,304 | 1/1995 | Parker . | |
| 5,409,469 | 4/1995 | Schaerf . | |
| 5,460,608 | 10/1995 | Lodin et al. | 604/96 |
| 5,472,435 | 12/1995 | Sutton . | |

FOREIGN PATENT DOCUMENTS

| | | | |
|---|---|---|---|
| 2017182 | 10/1979 | United Kingdom | 604/280 |

*Primary Examiner*—Corrine M. McDermott
*Assistant Examiner*—Deborah Blyveis
*Attorney, Agent, or Firm*—Michael J. Jaro; Harold Patton

[57] ABSTRACT

An introducer system featuring a sheath which is kink resistant. Such a sheath thereby permits the sheath to be dramatically bent while still allowing a lead to be introduced therethrough. The kink resistance is provided by a composite construction of the sheath. In particular the sheath has at least one integral reinforcing fiber. In the preferred embodiment the reinforcing fibers are provided in a braided configuration. The sheath preferably is constructed to be readily split using a slitter in a longitudinal direction and thus permits the sheath to be removed from the venous system without having to withdrawn the sheath over an end of the pacemaker lead. In an alternate embodiment the sheath is scored, including the reinforcing fibers, to thereby permit the sheath to be longitudinally split apart and removed from the venous system without having to withdrawn the sheath over an end of the pacemaker lead.

23 Claims, 10 Drawing Sheets

INTRODUCER SYSTEM HAVING KINK RESISTANT SPLITTABLE SHEATH

FIELD OF THE INVENTION

This invention relates generally to an introducer system having a kink resistant sheath for the insertion of catheters and other instruments into the body and more particularly to an introducer system having a kink resistant splittable sheath used to introduce pacemaker leads into the venous system.

BACKGROUND OF THE INVENTION

Generally speaking, pacing systems include an implantable pulse generator, commonly known as a pacemaker, electrically connected to the heart by at least one transvenous endocardial lead. More specifically an endocardial lead provides an electrical pathway between the pacemaker, connected to the proximal end of the lead, and endocardial tissue, in contact with the distal end of the lead. Endocardial tissue refers to a specific layer of tissue in the interior of the heart's chambers. In such a manner electrical pulses emitted by the pacemaker travel through the endocardial lead and stimulate the heart.

Endocardial leads are often placed in contact with the endocardial tissue by passage through a venous access, such as the subclavian vein or one of its tributaries. In such a manner transvenous endocardial leads offer as an advantage that they may be placed into contact with the heart without requiring major thoracic surgery. Rather, transvenous endocardial leads may be introduced into a vein and maneuvered therefrom into contact with the heart.

A multi-step procedure is often used to introduce such leads within the venous system. Generally this procedure consists of inserting a hollow needle into a blood vessel, such as the subclavian vein. A wire guide is then passed through the needle into the interior portion of the vessel. The needle is then withdrawn and an introducer sheath and dilator assembly is then inserted over the wire guide into the vessel. The assembly is advanced into a suitable position within the vessel, i.e. so that the distal end is well within the vessel but the proximal end is outside the patient. Next the dilator and wire guide are removed. The introducer sheath is left in position and therefore offers direct access from outside the patient to the interior of the blood vessel. In such a fashion a lead can be passed into the vessel through the introducer sheath and ultimately be positioned within the heart. Finally the introducer sheath is removed from the body. With respect to pacemaker leads, however, which typically have a relatively bulky connector pin assembly at the proximal end, the introducer sheath is removed from the body by being split apart. In such a manner the introducer sheath does not have to be removed over the relatively bulky connector pin assembly at the proximal end of the lead.

An introducer sheath therefore, through its hollow lumen, provides access to the interior of a vessel. A lead introduced into the blood vessel may then moved along the blood vessel until properly positioned within the heart.

To provide such access an introducer sheath must be flexible. Specifically, flexibility permits the introducer sheath to bend and form to a curve compatible with the blood vessel. In such a manner the introducer sheath end is substantially parallel to the blood vessel and a lead which is introduced therethrough is properly oriented along the vessel interior. If the sheath did not conform to the vessel shape, a lead introduced would abut against the vessel wall, possibly injuring the patient and damaging the lead. One problem which may occur, however, due to the flexibility required of the introducer sheath is that the mid-portion of the sheath may form a kink.

Kinking along the introducer sheath may cause serious problems, especially with respect to pacemaker leads. Generally a kink within an introducer sheath is not detected until a lead is attempted to be introduced therethrough. At that time the lead, and in particular the sensitive electrode at the distal end of the lead, strikes the kinked section and is blocked. Continual pushing on the lead may cause damage to the electrode as well as damage to the helical coil and insulative sheath of the lead body. Because such damage may not be readily apparent, implantation of a damaged lead may result, in turn, creating the possibility of serious harm to the patient.

A further problem exists in pacemaker patients who have had multiple leads implanted over time. Scar tissue at the site of implantation has been found to create difficulties with past lead introduction systems. Specifically the relatively tough scar tissue hinders the introduction of a dilator and introducer sheath assembly. Many times, only through use of larger incisions than are otherwise desirable is such an assembly able to be inserted.

Previously many have attempted to solve the problem of introducer kinking. For example, in U.S. Pat. No. 5,409,469 Schaerf proposed fitting at least a portion of the introducer sheath with a series of bellows or pleats. Such a design, however, failed to permit the introducer to be smoothly inserted into the tissue. As can be appreciated, the bellows or pleats give rise to a relatively large frictional drag of the sheath by the tissue. U.S. Pat. No. 5,380,304 of Parker disclosed the use of a flat wire coil to prevent kinking of an introducer. Such a design, however, did not permit the introducer sheath to be slit or split and thus removed from the lead disposed therethrough.

SUMMARY OF THE INVENTION

It is an object of the present invention to provide an introducer system having a sheath which is resistant to the formation of kinks.

It is a further object of the invention to provide an introducer system having a kink resistant sheath for introducing an elongated object into the venous system and especially for introducing a cardiac pacemaker lead.

It is a further object of the invention to provide an introducer system having a kink resistant sheath which minimizes the frictional drag of the sheath by the tissue as the sheath is inserted through the tissue.

It is a further object of the invention to provide an introducer system having a kink resistant sheath which permit the introducer sheath to be removed from the lead disposed therethrough without requiring the introducer sheath to be removed from an end of the lead disposed therethrough, by slitting or splitting the introducer sheath, for example.

These objects are met by the present invention which provides an introducer system featuring a sheath which is kink resistant. Such a sheath thereby permits the sheath to be dramatically bent while still allowing a lead to be introduced therethrough. The kink resistance is provided by a composite construction of the sheath. In particular the sheath has at least one integral reinforcing fiber. In the preferred embodiment the reinforcing fibers are provided in a braided configuration. The sheath preferably is constructed to be readily split using a slitter in a longitudinal direction and thus permits the sheath to be removed from the venous system without having to withdrawn the sheath over an end of the pacemaker lead. In an alternate embodiment the sheath is scored, including the reinforcing fibers, to thereby permit the sheath to be longitudinally split apart and removed from the venous system without having to withdrawn the sheath over an end of the pacemaker lead.

BRIEF DESCRIPTION OF THE DRAWINGS

The foregoing and other aspects of the present invention will be best appreciated with reference to the detailed description of the invention in conjunction with the accompanying drawings, wherein.

The drawings are not necessarily to scale.

DETAILED DESCRIPTION OF THE PREFERRED EMBODIMENT

It is to be understood, that the present invention is not limited to use only in introducing atrial or ventricular pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, the present invention may be employed in introducing many of various types of therapeutic or diagnostic catheters and is not limited only to the introduction of electrical leads. For purposes of illustration only, however, the present invention is below described in the context of the introduction of endocardial pacing leads.

Figure 1:
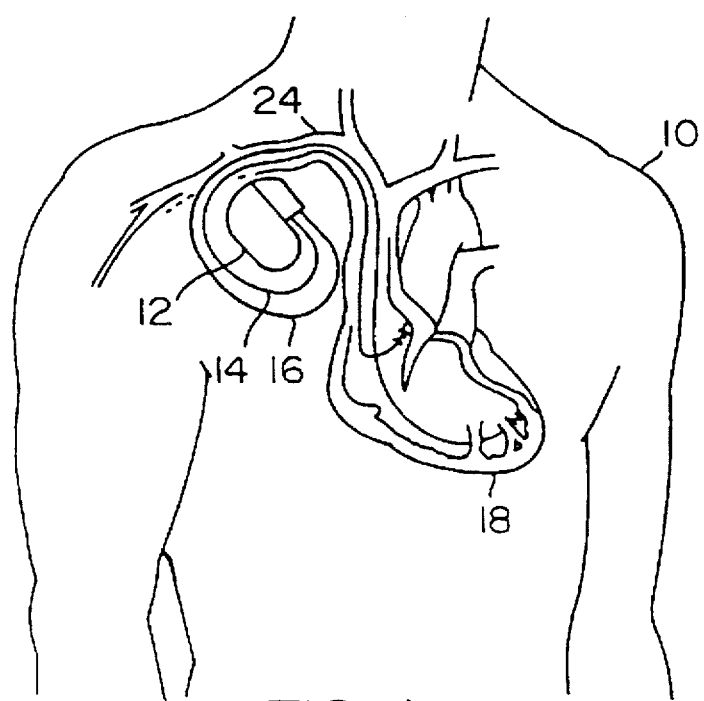
FIG. 1 depicts the venous positioning and placement of transvenous endocardial leads in a patient.

FIG. 1 depicts a typical arrangement of a pacing system implanted in a patient 10, the pacing system comprising a subcutaneously disposed pacemaker 12 and transvenous pacing leads 14 and 16. In FIG. 1, the distal end of pacing lead 14 is shown disposed generally in the atrial region of the patient's heart 18, while the distal end of pacing lead 16 is disposed generally in the ventricular region of heart 18.

The preferred prior art method of lead introduction compatible with an introducer system in accordance with the present invention will be described with reference to FIGS. 2 through 14.

Figure 2:
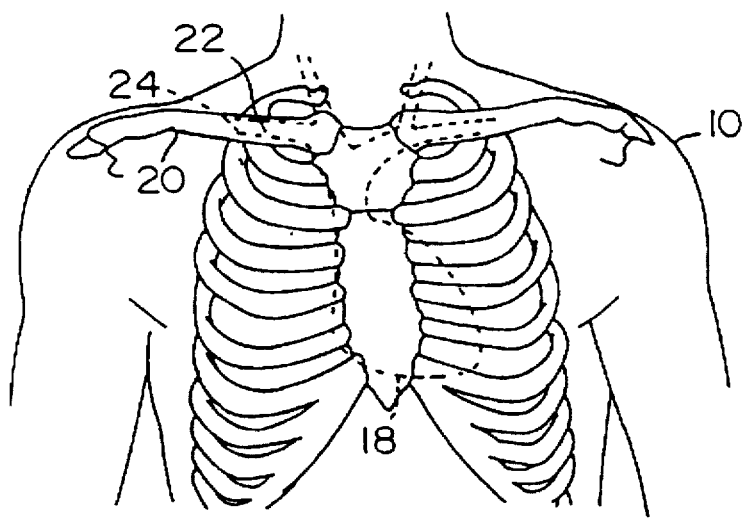
FIG. 2 depicts an appropriate entry site for implantation of a transvenous endocardial lead.

Referring to FIG. 2, and in accordance with common practice in the medical arts, the entry site for a subclavian vein puncture is commonly chosen to be just below and slightly medial to the junction of the middle and inner third of the clavicle 20, at an area designated generally as 22 in FIG. 2. In FIG. 2, the patient's subclavian vein 24 and heart 18 are shown in phantom.

Figure 3:
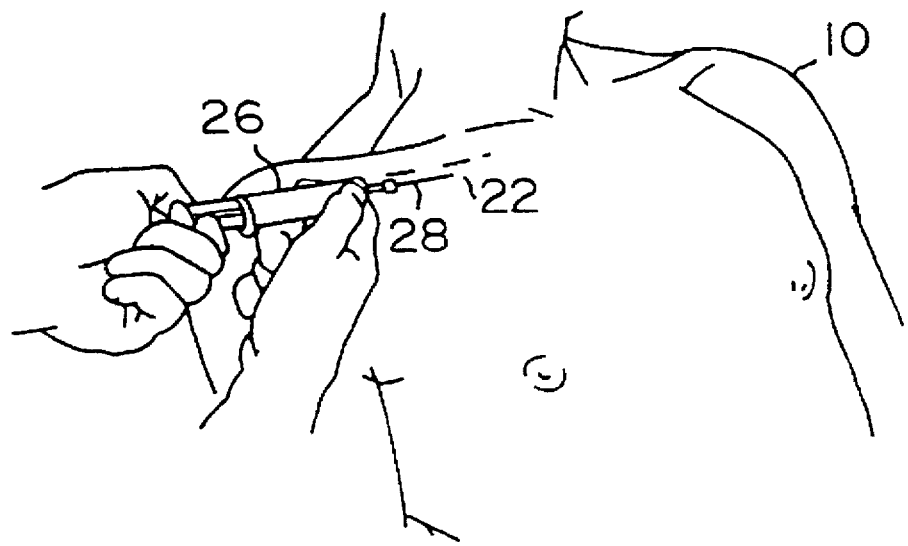
FIGS. 3–14 depict successive stages of introducing a transvenous endocardial lead into a vein.
Figure 4:
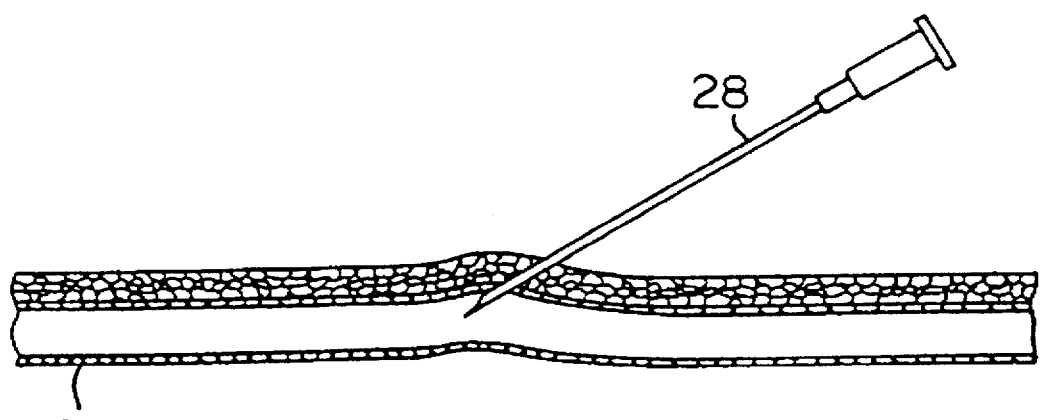

Turning to FIG. 3, the subclavian vein puncture is accomplished by the physician using a disposable syringe 26 having a thin-wall needle 28 detachably connected thereto. Aspiration is performed as the needle is advanced into the subclavian vein, to verify proper needle placement within vessel 24. Next, aspirating syringe 26 is disconnected from needle 28, which remains in vessel 24 as shown in FIG. 4. Typically, the physician will place his or her finger over the needle to avoid air aspiration and excessive bleeding.

Figure 5:
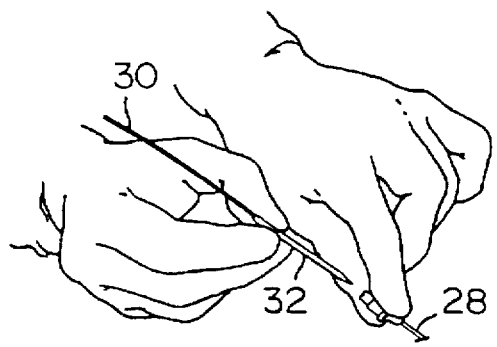
Figure 6:
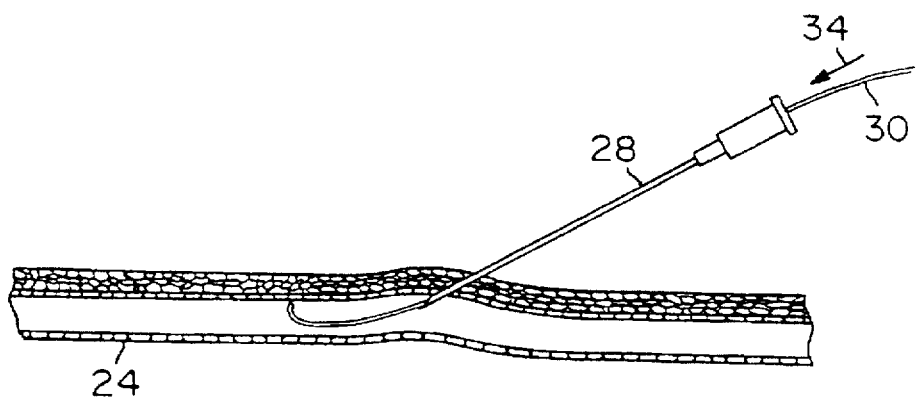
Figure 7:
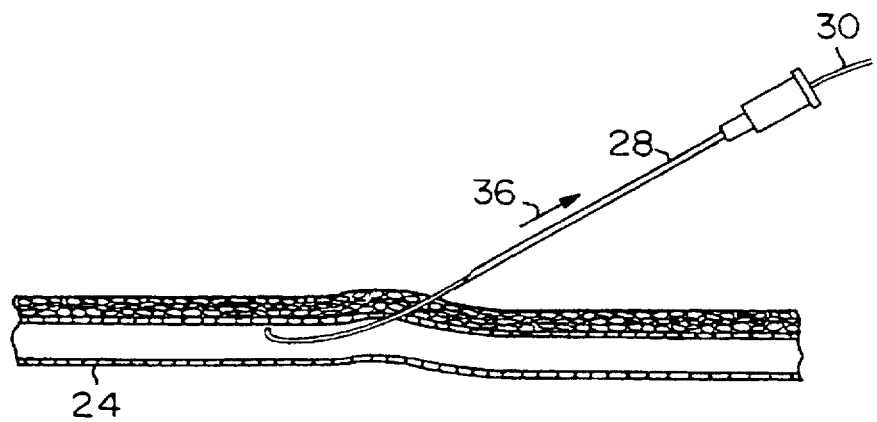

The next step in the lead implantation procedure involves insertion of a conventional J-type guide wire 30 through needle 28, as illustrated in FIG. 5. Typically, guide wire 30 is equipped with a tip deflector 32 for facilitating insertion of wire 30 into the lumen of needle 28. As shown in FIG. 6, as wire 30 is fed through needle 28 in the direction of arrow 34, the distal end of wire 30 exits the tip of needle 28, and wire 30 regains its "J" shape within vessel 24. Once wire 30 has entered vessel 24, needle 28 is withdrawn in the direction of arrow 36 in FIG. 7, leaving wire 30 in place. Wire 30 is advanced along vessel 24 until its distal end is disposed generally in the area of the patient's superior vena cava, leaving approximately 15 to 20-cm of the proximal end of wire 30 exposed.

Figure 8:
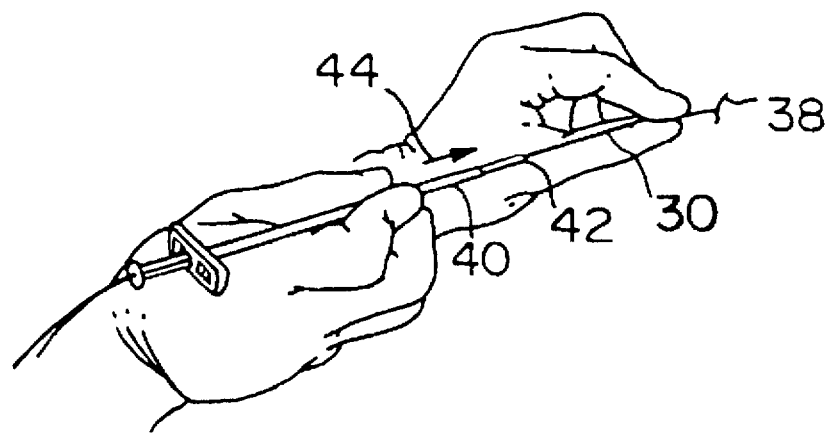
Figure 9:
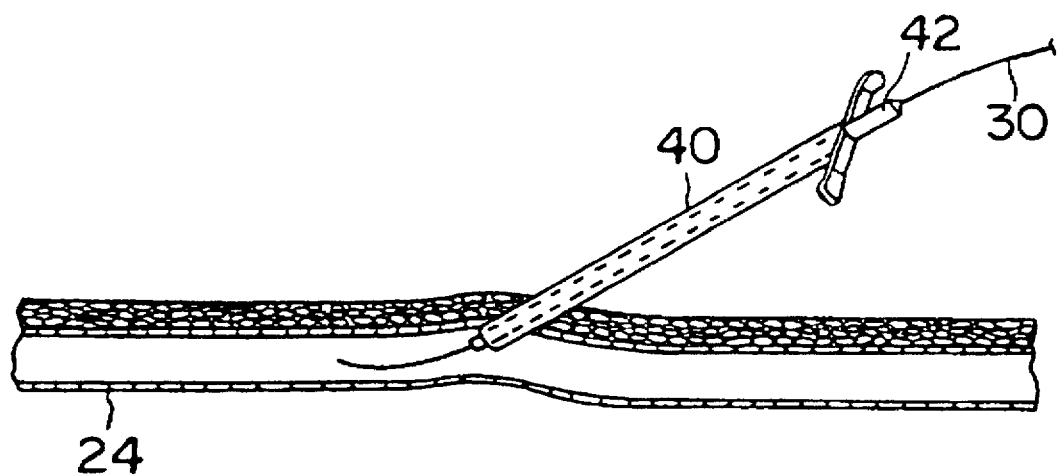

A small skin incision 38 is made at the guide wire entry site, parallel to clavicle 20, as shown in FIG. 8. In the next stage of the implantation procedure, an introducer sheath 40 with tapered vessel dilator 42, as an assembly, are threaded onto the proximal end of wire 30. Sheath 40 and dilator 42 are advanced in the direction of arrow 44, through the subclavian fascia and into subclavian vein 24, until a short length (e.g., 2 to 8-cm) of sheath 40 and vessel dilator 42 remain exposed, as shown in FIG. 9.

Figure 10:
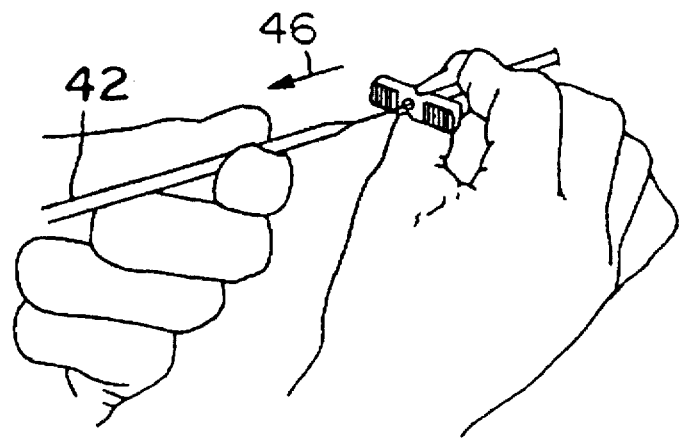
Figure 11:
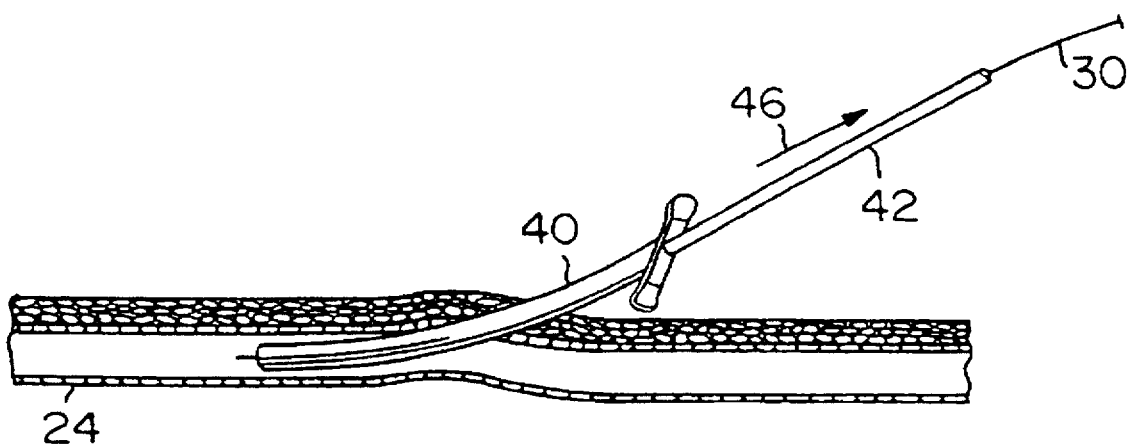

Next, as shown in FIGS. 10 and 11, vessel dilator 42 is withdrawn in the direction of arrow 46 and sheath 40 is introduced further within subclavian vein 24, leaving introducer sheath 40 and guide wire 30 in place with its distal end disposed within subclavian vein 24. Guide wire 30 may be removed at this point as well, although it may be left in place in case the lead needs to be repositioned or reinserted or an additional lead is to be implanted. As shown in FIG. 11, introducer sheath 40 must bend to conform to the shape of subclavian vein 24 to provide an unobstructed conduit for lead 14 to be introduced. Through such curvature, moreover, lead 14 may be introduced so as to be parallel to vein 24 and not abut and damage wall 25 of subclavian vein 24.

Figure 12:
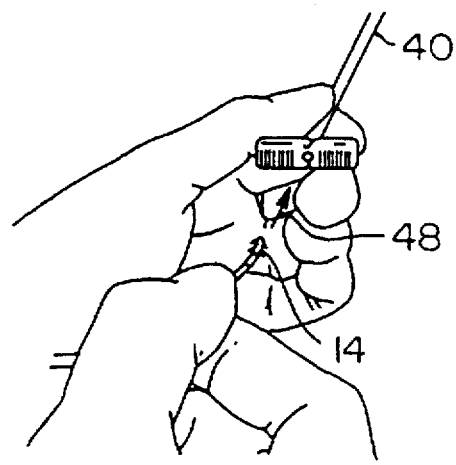
Figure 13:
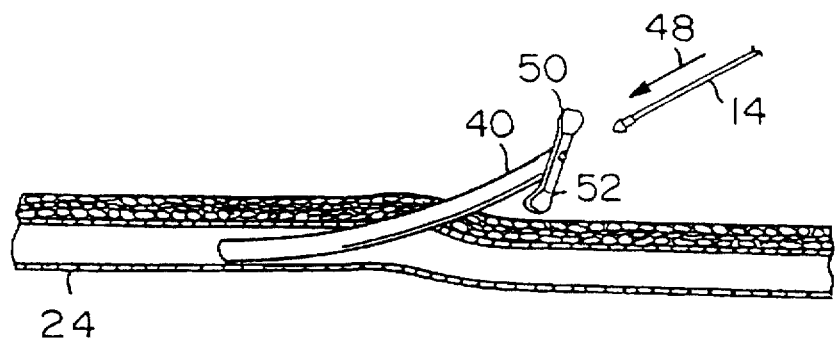
Figure 14:
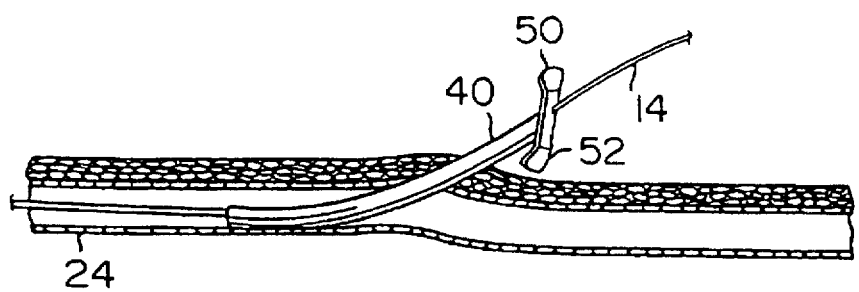

In the final stages of the lead implantation procedure, illustrated in FIGS. 12 through 14, pacing lead 14 is inserted into the proximal end of introducer sheath 40 in the direction of arrow 48, and advanced into the desired position within patient 10 through vessel 24. Lastly, introducer sheath 40 is removed. Removal of introducer sheath 40 may be accomplished in one of several known ways, depending upon the particular type of introducer sheath 40. For example, as disclosed in the above-noted Osborne '562 patent, sheath 40 may be longitudinally split by pulling tabs 50 and 52. Other sheaths are known which are severable by means of a special slitter device or the like.

As shown in FIG. 1, pacemaker 12 may operate in conjunction with two pacing leads. In that case, as with single-lead implants, it may be necessary to keep guide wire 30 in place until after the first lead has been implanted. Thus, as previously noted with reference to FIGS. 10 and 11, guide wire 30 may be left in place when dilator 42 is withdrawn. The first lead, if it is sufficiently small, may be introduced into subclavian vein 24 alongside guide wire 30, and then the first introducer sheath is removed leaving guide wire 30 in place. Then, a second introducer sheath and vessel dilator can be guided along guide wire 30 in the same manner as the first, before guide wire 30 is finally removed.

Figure 15:
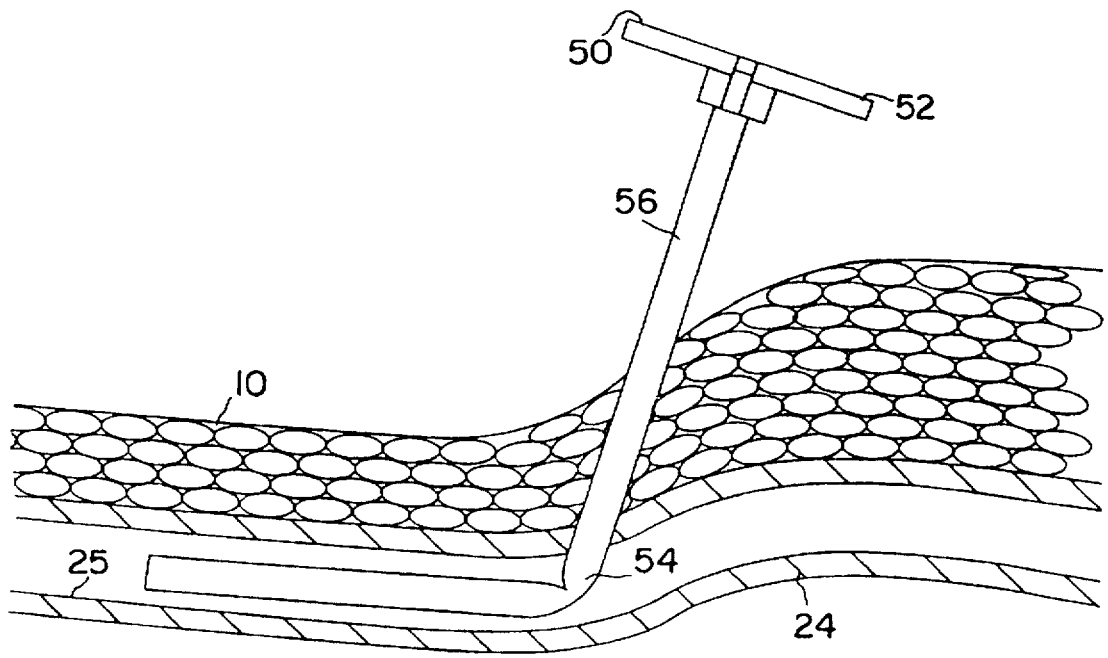
FIG. 15 depicts an introducer sheath used in a body and having a kink.

As depicted in FIG. 15 one problem associated with lead introduction systems and particularly with the sheath used in previous lead introduction systems is the formation of a kink 54. As seen a kink 54 in sheath 56 prevents lead 14 from being introduced therethrough. As mentioned such kinks may be undetected so that a lead inserted into the sheath is blocked, possibly resulting in damage to the lead.

Figure 16:
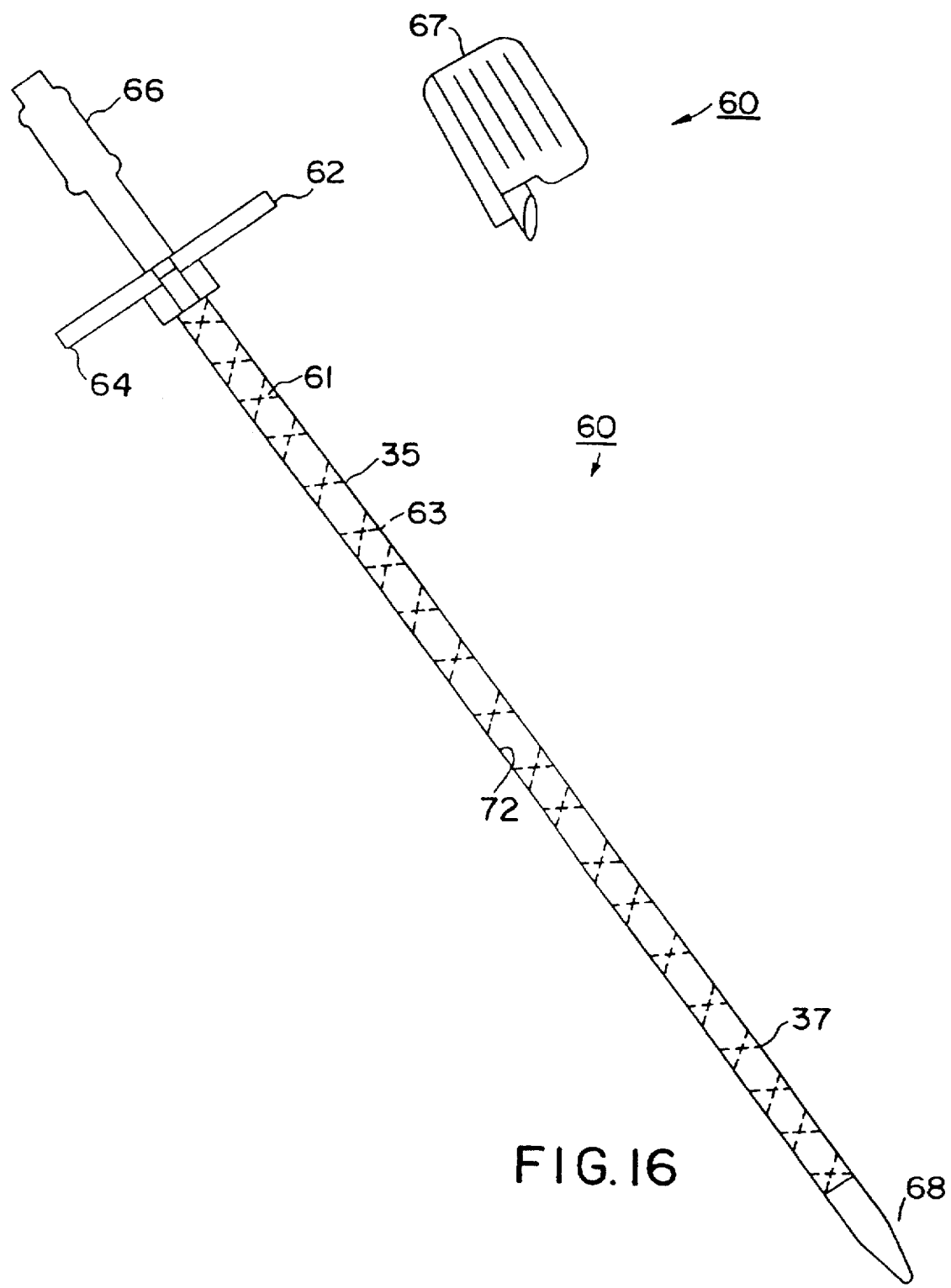
FIG. 16 depicts a lead introducer system in accordance with one embodiment of the present invention.

Turning now to FIG. 16, an introducer system 60 in accordance with one embodiment of the present invention is illustrated. Introducer system 60 comprises an introducer sheath 61 in which a vessel dilator 66 is inserted. A tapered end 68 of vessel dilator 66 facilitates the introduction of sheath 60 into the subclavian vessel 24. Thereafter, guide wire 30 and vessel dilator 66 are withdrawn from the patient and central lumen 65 within sheath 61 provides access to the vessel 24.

As seen introducer system 60 features a sheath 61 which is kink resistant. Kink resistance is important because it permits the sheath to be dramatically bent while still allowing a lead to be introduced therethrough. The kink resistance is provided by the composite construction of the sheath. That is, sheath 61 has a two-part construction with a tubular portion 71 having at least one reinforcing fiber 72 integral therewith. In the preferred embodiment reinforcing fibers 72 are provided in a braided configuration with more than one fiber in parallel wound together, the fibers being wound between 20–45 pics per inch, with 32 pics per inch preferred. Fibers 72 are preferably a high strength polymer fiber, such as nylon. Tubular portion of sheath is made of a biocompatible plastic, such as low density polyethylene. A suitable composite sheath 61 having a tubular portion 71 with reinforcing fibers 72 integral therewith is available from TFX Medical, Limerick, Ireland.

One important benefit of the sheath of the present invention is that it permits either a thinner walled sheath to be utilized which would have the same kink resistance as compared to a same sized sheath without the reinforcing fibers, or an overall more flexible material to be used for the sheath as compared to a same sized sheath without the reinforcing fibers. The use of a thinner walled sheath is of benefit because it reduces the total sheath diameter and thus reduces the incision into the patient's venous system. The use of a more flexible material is of benefit because it provides for a sheath which is less likely to jab into and damage to venous system of the patient.

In the embodiment of FIG. 16, sheath 61 includes means for permitting removal of sheath 61 from a lead disposed therethrough without requiring sheath 61 to be removed from an end of the lead. Specifically sheath 61 may be removed from a pacing lead by being longitudinally slit apart using a sheath slitter 67. As seen a pair of separable tabs 62, 64 are mounted to the proximal end of sheath 61 to facilitate both the introduction of the sheath as well as the removal of the sheath from about the lead.

Figure 17:
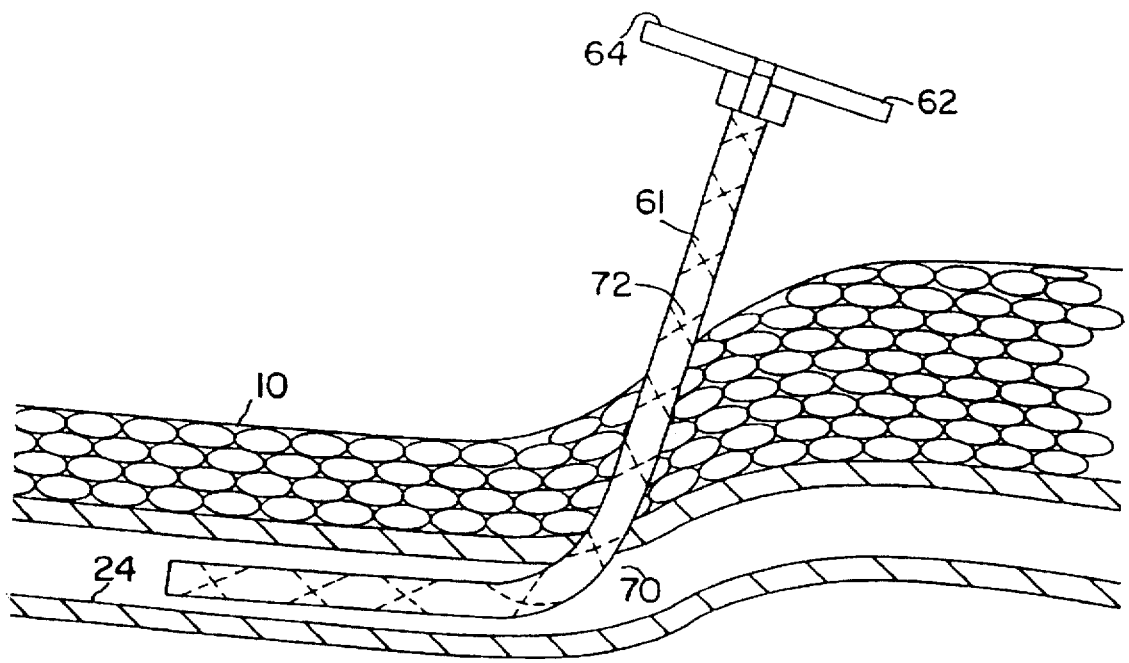
FIG. 17 depicts an introducer sheath of the present invention used in a body and not having a kink.

As depicted in FIG. 17 the lead introduction system of the present invention and particularly kink resistant sheath 61 may be dramatically bent without a kink being formed. As mentioned above, such kinks may be undetected so that a lead inserted into the sheath is blocked by the kink and cannot be inserted any further. Such a situation may result in damage to the lead.

Figure 18:
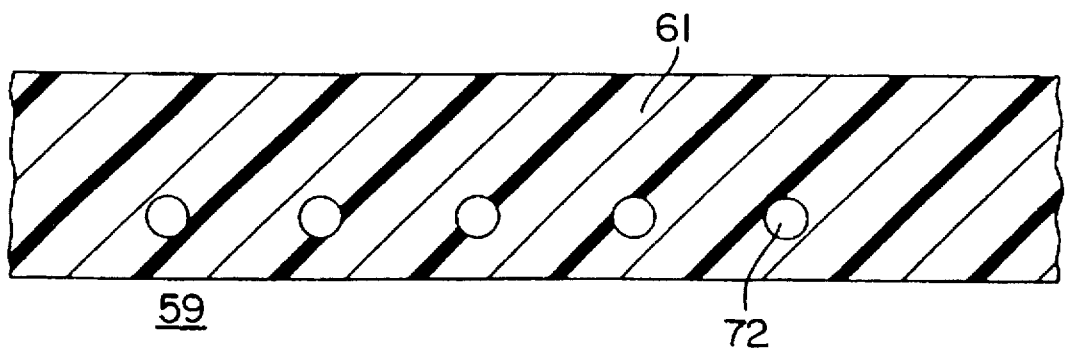
FIG. 18 is a detailed cross-sectional view of the wall of the kink resistant sheath used in an introducer system of the present invention.

FIG. 18 is a detailed cross-sectional view of the wall of the kink resistant sheath used in an introducer system of the present invention. As seen sheath 61 has reinforcing fibers 72 disposed in the approximate middle portion of the sheath wall.

Figure 19:
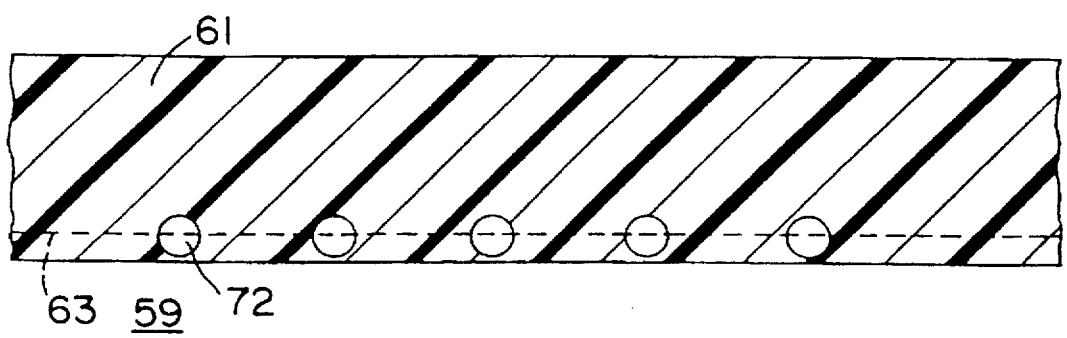
FIG. 19 is a detailed cross-sectional view of an alternate embodiment of the wall of the kink resistant sheath used in an introducer system of the present invention.

FIG. 19 is a detailed cross-sectional view of an alternate embodiment of the wall of the kink resistant sheath used in an introducer system of the present invention. As seen sheath 61 has reinforcing fibers 72 disposed in the inner portion of the sheath wall closer to the sheath lumen 59. This embodiment further features a score line 63 cut into both the sheath wall and the reinforcing fibers 72. This permits sheath 61 to be longitudinally split apart along score line 63 by grasping and pulling apart tabs 62 and 64 as sheath 61 is being withdrawn from the lead introduction site. Various other equivalent means may also be used to accomplish splitting sheath 61 along line 63, these include by providing a line of weakened wall, as shown in Vegoe et al U.S. Pat. No. 5,180,372, incorporated herein by reference, or the entire wall could be constructed using material having the physical property of molecular orientation whereby a tear in the material runs readily only in a longitudinal direction along the length of sheath 61, as is well known in the art.

Figure 20:
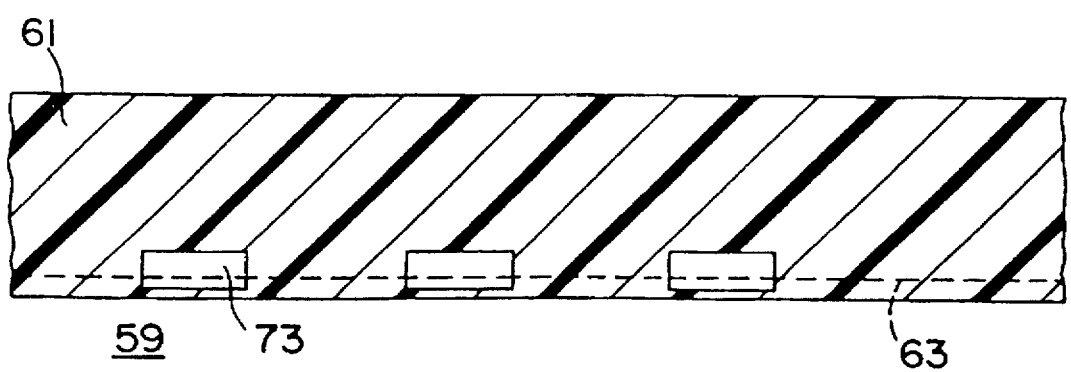
FIG. 20 is a detailed cross-sectional view of an alternate embodiment of the wall of the kink resistant section used in an introducer system of the present invention.

FIG. 20 is a detailed cross-sectional view of an alternate embodiment of the wall of the kink resistant sheath used in an introducer system of the present invention. As seen sheath 61 has non symmetrical reinforcing fibers 73 disposed in the inner portion of the sheath wall closer to the sheath lumen 59. As shown, the non symmetrical reinforcing fibers 73 are rectangular in cross section. This shape causes the ratio between axial torque and radial bending stiffness to be modified so that the surface moment of inertia along or parallel to the coil axis is less than the surface moment of inertia along a radial axis in the same coil. Of course other shapes may also be used, such as elliptical, trapezoidal or oval so long as the dimension of the fiber measured parallel to the fiber axis is larger than the dimension measured radially. This embodiment further features a score line 63 cut into both the sheath wall and the reinforcing fibers 72 to permit sheath 61 to be longitudinally split apart along score line 63 by grasping and pulling apart tabs 62 and 64 as sheath 61 is being withdrawn from the lead.

In the preferred embodiment, the introducer system of the present invention is sterilized using ethylene oxide and packaged as a kit with a sterilized percutaneous needle 28, a guide wire 30, syringe 26 and a dilator 42 in a hermetically sealed plastic bag (not shown.)

Figure 21:
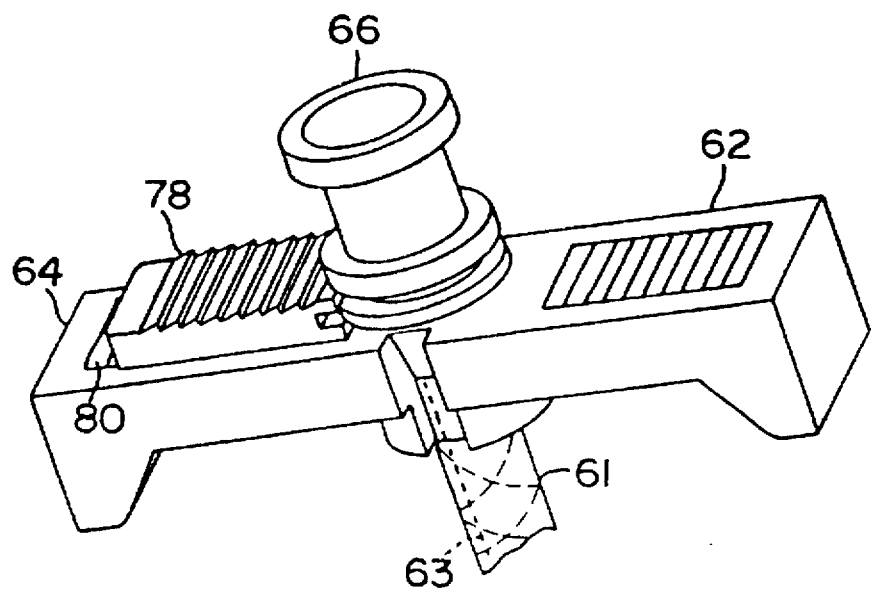
FIGS. 21 and 22 depict a detailed view of the distal end of an alternate embodiment of a lead introducer system featuring a sliding cap which may be incorporated with the present invention.
Figure 22:
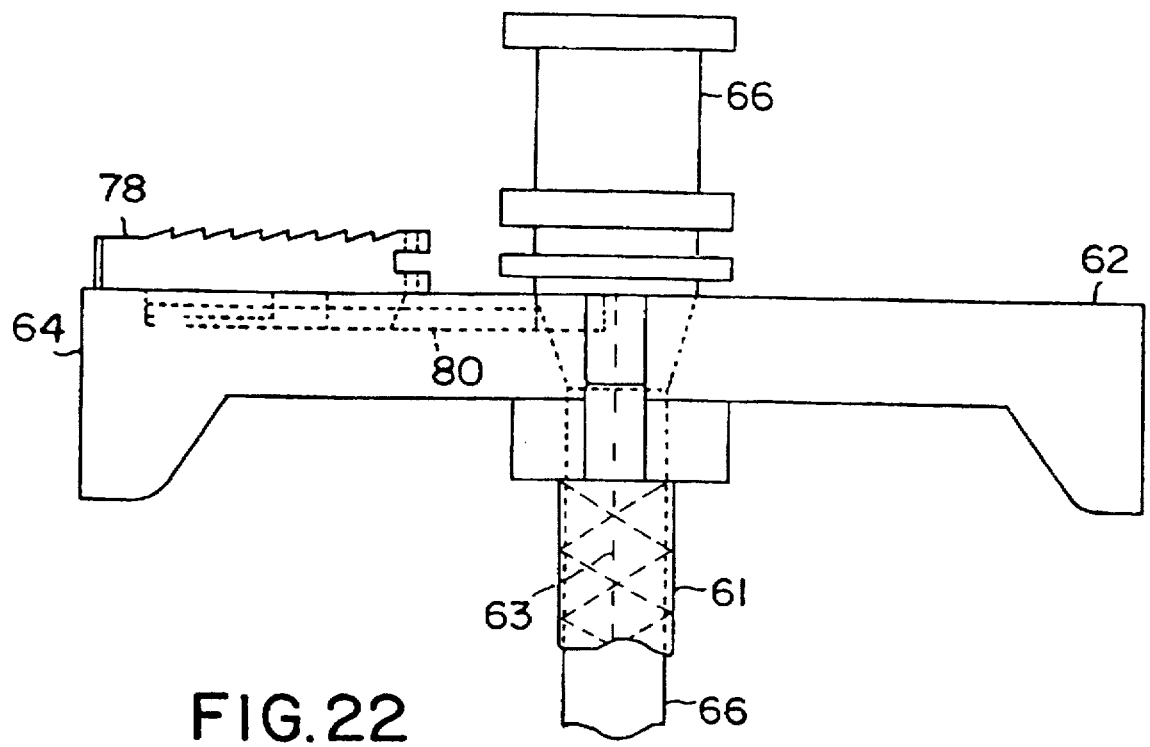

FIGS. 21 and 22 depict a still further alternate embodiment of the present invention. Specifically this embodiment features a device to inhibit blood flow through the sheath when a lead is not positioned within the lumen. As seen cap 78 is positioned within recess 80 so as to slide across the proximal end of sheath 61, and specifically between tabs 62 and 64, and cover the lumen within sheath 61 present when dilator 66 is withdrawn. Further details concerning the construction of such a device may be seen in the U.S. Pat. No. 5,441,504 of Pohndorf and incorporated herein by reference.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. An introducer system for use with a catheter or lead comprising:

a sheath having a first end and a second end, the sheath being compatible for insertion within a body, the first end configured to insert the sheath within the body with the second end extending out of the body, a pair of separable tabs mounted to the second end, the sheath having a central lumen configured to permit introduction of at least one lead or catheter therethrough the sheath having at least one reinforcing fiber;

means for permitting removal of the sheath from the lead or catheter disposed therethrough without requiring the sheath to be removed over an end of the lead or catheter disposed therethrough; and a dilator having a first end and a second end, the first end of the dilator being tapered, the dilator configured to be disposed through the central tureen of the sheath.

2. The introducer system of claim 1 wherein the means for permitting removal of the sheath comprises means for splitting the sheath away from the lead or catheter disposed therethrough.

3. The introducer system of claim 2 wherein the means for splitting the sheath comprises a weakened section extending longitudinally from the first end to the second end of the sheath.

4. The introducer system of claim 3 wherein the weakened section comprises a score line.

5. The introducer system of claim 3 wherein the weakened section comprises a section of material having the physical property of molecular orientation whereby a tear in the material runs readily only in a longitudinal direction along the length of the sheath.

6. The introducer system of claim 2 wherein the means for splitting the sheath comprise a first tab on a first side of the second end of the sheath, and a second tab on a second side of the second end of the sheath whereby, when the tabs are pulled apart, the sheath tears longitudinally separating the sheath from the lead or catheter disposed therethrough.

7. The introducer system of claim 1 wherein the sheath is a plastic.

8. The introducer system of claim 1 wherein the sheath is low density polyethylene.

9. The introducer system of claim 1 wherein the reinforcing fiber is circular in cross section.

10. The introducer system of claim 1 wherein the reinforcing fiber is rectangular in cross section.

11. The introducer system of claim 1 wherein the reinforcing fiber in cross section has a major dimension and a minor dimension, the major dimension parallel to the lumen of the sheath.

12. An introducer system for use with a catheter or lead comprising:

a sheath having a first end and a second end, the sheath having a wall, the wall defining a central lumen through the sheath, the wall having a thickness, a pair of separable tabs mounted to the second end of the sheath, the central lumen configured to permit introduction of at least one lead or catheter therethrough, the sheath having at least one reinforcing fiber, the reinforcing fiber mounted within the wall;

means for permitting removal of the sheath from the lead or catheter disposed therethrough without requiring the sheath to be removed over an end of the lead or catheter disposed therethrough; and a dilator having a first end and a second end, the first end of the dilator being tapered, the dilator configured to be disposed through the central lumen of the sheath.

13. The introducer system of claim 12 wherein the the reinforcing fiber is mounted within the wall at a point between an exterior surface of the wall and a interior surface of the wall.

14. The introducer system of claim 13 wherein the point is equally between an exterior surface of the wall and a interior surface of the wall.

15. The introducer system of claim 12 wherein the reinforcing fiber is mounted within the wall at a point along the interior surface of the wall.

16. The introducer system of claim 12 wherein the means for permitting removal of the sheath comprises means for splitting the sheath away from the lead or catheter disposed therethrough.

17. The introducer system of claim 12 wherein the means for splitting the sheath comprise a first tab on a first side of the second end of the sheath, and a second tab on a second side of the second end of the sheath, the reinforcing fiber is mounted within the wall at a point along the the interior surface of the wall, the wall and the reinforcing fiber have a score line whereby when the tabs are pulled apart, the sheath tears longitudinally separating the sheath from the lead or catheter disposed therethrough along the score line.

18. The introducer system of claim 12 in which the sheath is low density polyethylene.

19. An introducer kit comprising:

a sheath having a first end and a second end, the first end having means for inserting the sheath within the body with the second end extending out of the body, the sheath configured to permit introduction of at least one lead or catheter therethrough, a pair of separable tabs mounted to the second end, the sheath having a central lumen configured to permit introduction of at least one lead or catheter therethrough the sheath having at least one reinforcing fiber;

means for permitting removal of the sheath from the lead or catheter disposed therethrough without requiring the sheath to be removed over an end of the lead or catheter disposed therethrough;

a percutaneous needle;

a wire guide; and a dilator.

20. The introducer system of claim 19 wherein the means for splitting the sheath comprise a first tab on a first side of the second end of the sheath, and a second tab on a second side of the second end of the sheath, whereby when the tabs are pulled apart, the sheath tears longitudinally separating the sheath from the lead or catheter disposed therethrough.

21. The introducer system of claim 20 wherein the weakened section comprises a score line.

22. The introducer system of claim 20 wherein the weakened section comprises a section of material having the physical property of molecular orientation whereby a tear in the material runs readily only in a longitudinal direction along the length of the sheath.

23. The introducer system of claim 19 wherein the means for splitting the sheath comprises a weakened section extending longitudinally from the first end to the second end of the sheath.

* * * * *